(12) United States Patent
Shibuya et al.

(10) Patent No.: US 8,989,350 B2
(45) Date of Patent: Mar. 24, 2015

(54) CONTROL APPARATUS OF RADIOTHERAPY SYSTEM AND OPERATION METHOD OF RADIOTHERAPY SYSTEM

(75) Inventors: Osamu Shibuya, Tokyo (JP); Yoshimi Oda, Tokyo (JP); Kunio Takahashi, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 449 days.

(21) Appl. No.: 13/266,848

(22) PCT Filed: Oct. 26, 2010

(86) PCT No.: PCT/JP2010/068928
§ 371 (c)(1),
(2), (4) Date: Jan. 18, 2012

(87) PCT Pub. No.: WO2011/102018
PCT Pub. Date: Aug. 25, 2011

(65) Prior Publication Data
US 2012/0134470 A1      May 31, 2012

(30) Foreign Application Priority Data

Feb. 17, 2010    (JP) .................................. 2010-032853

(51) Int. Cl.
*A61N 5/10*       (2006.01)
*A61B 6/08*       (2006.01)
*H05G 1/02*       (2006.01)

(52) U.S. Cl.
CPC ....... *A61N 5/1065* (2013.01); *A61N 2005/1061* (2013.01)
USPC ................................ 378/65; 378/95; 378/205

(58) Field of Classification Search
CPC ............. A61N 5/00; A61N 5/01; A61N 5/10; A61N 5/1048; A61N 5/1064; A61N 5/1065; A61N 5/1077
USPC ............... 378/65, 91–95, 193, 196, 197, 204, 378/205, 207, 210
See application file for complete search history.

(56) References Cited

U.S. PATENT DOCUMENTS

2007/0211857 A1    9/2007    Urano et al.
2007/0244386 A1    10/2007   Steckner et al.

FOREIGN PATENT DOCUMENTS

| CN | 101032651 | 9/2007 |
|---|---|---|
| EP | 1 832 313 | 9/2007 |

(Continued)

OTHER PUBLICATIONS

International Search Report issued Nov. 22, 2010 in International (PCT) Application No. PCT/JP2010/068928.
International Preliminary Report on Patentability and Written Opinion of the International Searching Authority issued Sep. 18, 2012 in International (PCT) Application No. PCT/JP2010/068928.
Japanese Decision to Grant a Patent dated Apr. 4, 2013 in corresponding Japanese Patent Application No. 2010-032853 with English translation.

(Continued)

*Primary Examiner* — Anastasia Midkiff
(74) *Attorney, Agent, or Firm* — Wenderoth, Lind & Ponack, L.L.P.

(57) ABSTRACT

A control apparatus of a radiotherapy system of the present invention includes an irradiation object detecting section configured to calculate a target position based on a position of a specific part of a sample; and a swing position control section configured to control a drive unit to drive a radiation irradiating unit which irradiates a therapeutic radiation, such that the radiation irradiating unit directs to a post-correction target position at a control time after the measurement time. The post-correction target position indicates a position near a position to which the radiation irradiating unit directs rather than the target position in the preparation period before a therapy period, and the target position in the therapy period.

12 Claims, 9 Drawing Sheets

(56) References Cited

FOREIGN PATENT DOCUMENTS

| | | |
|---|---|---|
| JP | 2004-65808 | 3/2004 |
| JP | 2006-21046 | 1/2006 |
| JP | 2006-51199 | 2/2006 |
| JP | 2007-507275 | 3/2007 |
| JP | 2007-236760 | 9/2007 |

OTHER PUBLICATIONS

Chinese Office Action issued Feb. 11, 2014 in corresponding Chinese Patent Application No. 201080022111.2 with English translation.

Extended European Search Report issued Apr. 9, 2014 in corresponding European Patent Application No. 10846150.0.

Decision to Grant a Patent in corresponding Chinese Patent Application No. 201080022111.2 dated Sep. 3, 2014.

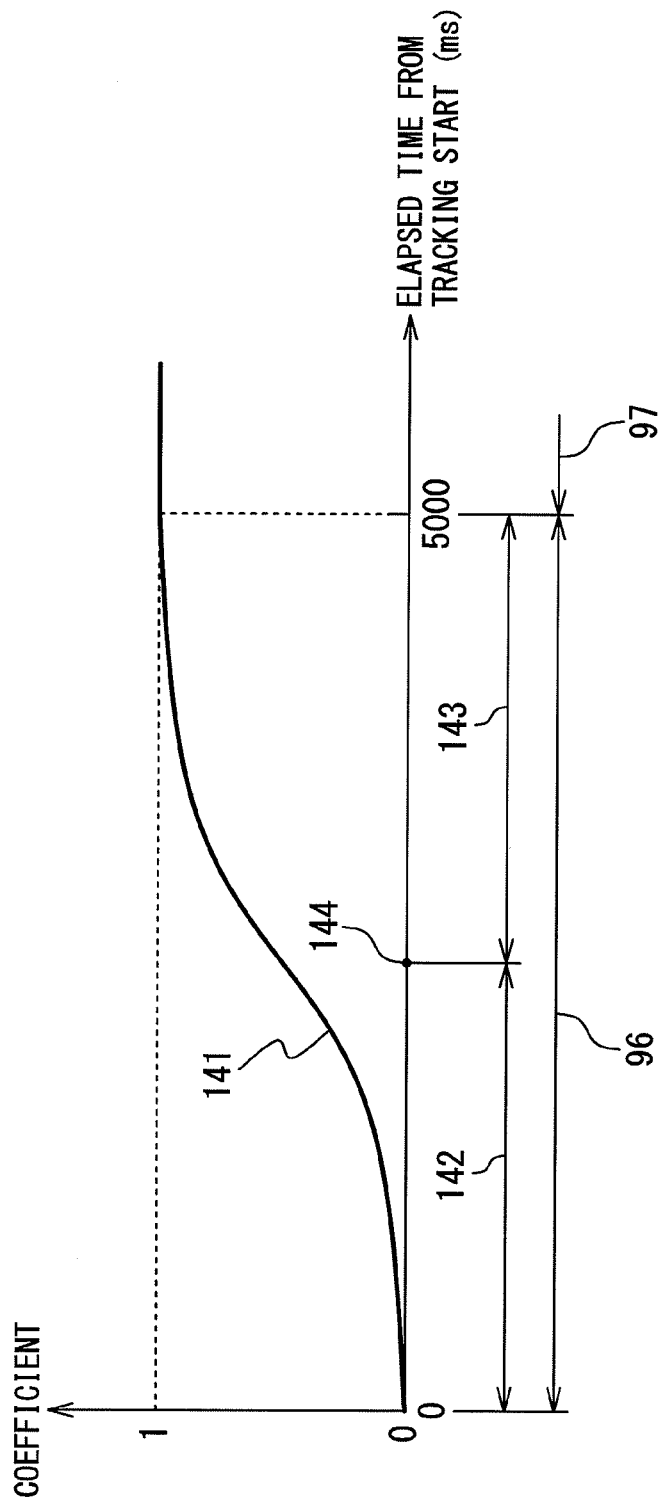

CONTROL APPARATUS OF RADIOTHERAPY SYSTEM AND OPERATION METHOD OF RADIOTHERAPY SYSTEM

TECHNICAL FIELD

The present invention is related to a control apparatus of a radiotherapy system and an operation method of the radiotherapy system. Especially, the present invention is related to a control apparatus of a radiotherapy system and an operation method of the radiotherapy system which is used to cure a patient by irradiating radiation to an affected part.

BACKGROUND ART

Radiotherapy is known which cures a patient by irradiating therapeutic radiation to an affected part of tumor. The radiotherapy system which carries out radiotherapy is provided with a therapeutic radiation irradiating unit which irradiates the therapeutic radiation, a sensor which measures a position of the affected part of the patient, and a drive unit which moves the therapeutic radiation irradiating unit such that the therapeutic radiation is irradiated to the measured position. According to such a radiotherapy system, even when the affected part moves with a breathing operation of the patient, the therapeutic radiation can be irradiated surely to the affected part. In such radiotherapy, it is demanded that the therapy effect is high. Also, it is demanded that a quantity of the therapeutic radiation irradiated to normal cells is smaller than the radiation quantity is irradiated to cells in the affected part. For this reason, it is demanded that the radiotherapy system irradiates the therapeutic radiation to the affected part in a high accuracy and moves the therapeutic radiation irradiating unit in a high accuracy. Moreover, in the radiotherapy system, it is demanded that the responsibility of the drive unit is high and moreover that the operation of the drive unit is stable.

In JP 2004-65808A, the radiotherapy system is disclosed which forms a radiation field from a wide radiation field to a minute unshaped radiation field, which is possible to reduce an irradiation time and appropriately irradiate according to movement of the body of the patient, and which is possible to have a small size. The radiotherapy system is provided with an electron beam generating source, a deflection electromagnet which changes a direction of the electron beam, a vacuum window configured to pass the electron beam while holding the vacuum state, a scattering foil configured to scatter the electron beam, a target which converts the electron beam into an X-ray, a flattening filter circuit configured to make dose distributions of the electron beam and the X-ray uniform in the irradiation plane, collimators which collimate the electron beam and an X-ray, an irradiation head having dosimeters configured to measure the doses of the X-ray and the electron beam, and a gantry arm which supports the irradiation head. The radiotherapy system further contains a rotating unit couples the electron beam source and the deflection electromagnet by a vacuum rotary joint, and swings the irradiation head with respect to an axis parallel to a gantry arm rotation axis and passing a virtual source position.

In JP 2006-21046A, a radiotherapy system is disclosed which the condition of a therapeutic field can be monitored in real time even during radiotherapy. The radiotherapy system is provided with an O-type gantry, a radiation irradiating head which is provided rotatably for the O-type gantry, to irradiate a therapeutic radiation to the therapeutic field, an X-ray source which is provided movably for the O-type gantry, to irradiate a diagnostic X-ray to the therapeutic field, and sensor arrays which are provided movably for the O-type gantry, to generate diagnostic images by detecting the diagnostic X-rays passing through the sample. The sensor arrays are provided on symmetrical positions with respect to the radiation irradiating head, to move on the O-type gantry in conjunction with the movement of the radiation irradiating head, and the X-ray source moves in response to the movement of the sensor arrays.

CITATION LIST

[Patent Literature 1]: JP 2004-65808A
[Patent Literature 2]: JP 2006-21046A

SUMMARY OF THE INVENTION

A subject matter of the present invention is to provide a control apparatus of a radiotherapy system and an operation method of the radiotherapy system, in which it is possible to prevent a motor trip of a drive unit for moving a radiation irradiating unit which irradiates a therapeutic radiation, and it is possible to move the radiation irradiating unit in a high accuracy.

The control apparatus of a radiotherapy system includes an irradiation object detecting section configured to calculate a target position based on a position of a specific part of a sample at a measurement time; and a swing position control section configured to control a drive unit to drive a radiation irradiating unit which irradiates a therapeutic radiation, such that the radiation irradiating unit turns to a post-correction target position at a control time after the measurement time. The post-correction target position indicates a position near a position to which the radiation irradiating unit turns immediately before the control time rather than the target position, when the control time is contained in the preparation period. The post-correction target position indicates the target position when the control time is contained in a therapy period after the preparation period. Such a control apparatus of the radiotherapy system can prevent from the motor trip of the drive unit and can move the radiation irradiating unit in a high accuracy, by controlling the drive unit to track the specific part after controlling the drive unit to move the radiation irradiating unit slowly.

The post-correction target position indicates a position of an internal division of a segment linking an initial position and the target position when the control time is contained in the preparation period. At this time, a ratio of the internal division of the segment by the post-correction target position is desirably calculated such that the post-correction target position gradually approaches to the target position with elapse of time.

It is desirable that a change per a unit time of the internal division ratio is constant.

The swing position control section includes an operation amount calculating section configured to calculate an operation amount based on a position deviation between the post-correction target position and the position to which the radiation irradiating unit directs; a coefficient calculating section configured to calculate a coefficient based on the position deviation; and a multiplier configured to calculate a post-correction operation amount by multiplying the operation amount by the coefficient. The coefficient decreases constantly with respect to an absolute value of the position deviation. It is desirable that the drive unit is controlled based on the post-correction operation amount.

The swing position control section further includes a feed-forward section configured to calculate a feed-forward operation amount based on a change of the post-correction target position. The drive unit is controlled based on the feed-forward operation amount in addition to the post-correction operation amount.

The swing position control section further includes a temperature drift correcting section configured to calculate a temperature drift amount based on a temperature of a unit which generates an electrical signal supplied to the drive unit when the drive unit is controlled. It is desirable that the drive unit is controlled based on the temperature drift amount in addition to the feed-forward operation amount and the post-correction operation amount.

An operation method of a radiotherapy system according to the present invention includes: calculating a target position based on a position of a specific part of a sample at a measurement time; and controlling a drive unit to drive a radiation irradiating unit which irradiates a therapeutic radiation, such that the radiation irradiating unit directs to a post-correction target position at a control time after the measurement time. The post-correction target position indicates a position nearer a position to which the radiation irradiating unit turns immediately before the control time rather than the target position, when the control time is contained in the preparation period. The post-correction target position indicates the target position, when the control time is contained in a therapy period after the preparation period. According to the operation method of the radiotherapy system, the control apparatus of the radiotherapy system can prevents the motor trip of the drive unit and can move the radiation irradiating unit in a high accuracy, by controlling the drive unit to track the specific part after controlling the drive unit to move the radiation irradiating unit slowly.

The post-correction target position indicates a position of an internal division of a segment linking an initial position and the target position when the control time is contained in the preparation period. A ratio of the internal division of the segment by the post-correction target position is calculated such that the post-correction target position gradually approaches to the target position with elapse of time.

It is desirable that a change per a unit time of the internal division ratio is constant.

The operation method of the radiotherapy system further includes: calculating an operation amount based on a position deviation between the post-correction target position and the position to which the radiation irradiating unit turns; calculating a coefficient based on the position deviation; and calculating a post-correction operation amount by multiplying the operation amount by the coefficient. The coefficient decreases constantly with respect to an absolute value of the position deviation. It is desirable that the drive unit is controlled based on the post-correction operation amount.

The operation method of the radiotherapy system further includes: calculating a feed-forward operation amount based on a change of the post-correction target position. It is desirable that the drive unit is controlled based on the feed-forward operation amount in addition to the post-correction operation amount.

The operation method of the radiotherapy system further includes: calculating a temperature drift amount based on a temperature of a unit which generates an electrical signal supplied to the drive unit when the drive unit is controlled. It is desirable that drive unit is controlled based on the temperature drift amount in addition to the feed-forward operation amount and the post-correction operation amount.

The control apparatus and the radiotherapy system and the operation method of the radiotherapy system by the present invention can prevent the motor trip of the drive unit for driving the radiation irradiating unit and can move the radiation irradiating unit in the high accuracy, when the radiation irradiating unit which irradiates a therapeutic radiation is moved.

BRIEF DESCRIPTION OF THE DRAWINGS

FIG. 10 is a graph showing a change of another coefficient calculated by the target position correcting section.

DESCRIPTION OF EMBODIMENTS

Figure 1:
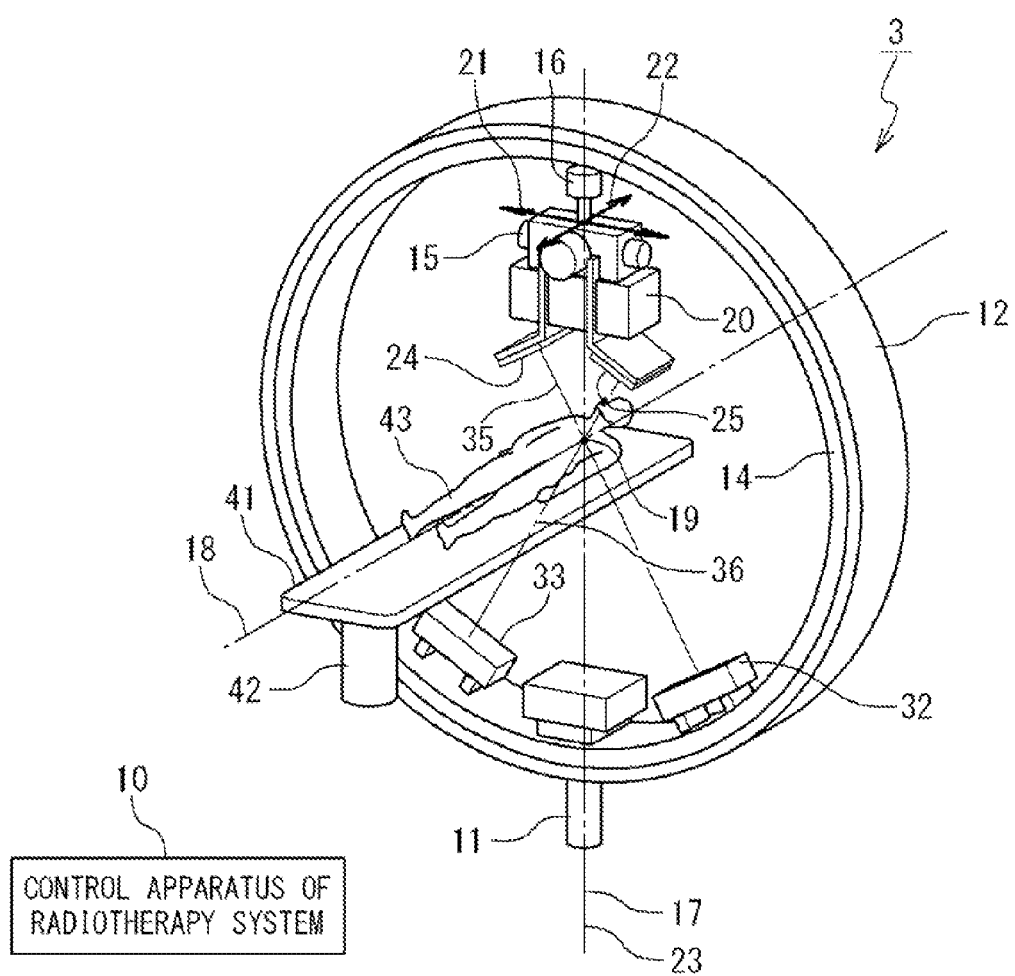
FIG. 1 is a perspective view showing a radiotherapy system.

Hereinafter, a control apparatus of a radiotherapy system according to the present invention will be described in detail with reference to the attached drawings. As shown in FIG. 1, the control apparatus 10 is applied to the radiotherapy system. The radiotherapy system is provided with the control apparatus 10 and a radiotherapy apparatus 3. The control apparatus 10 is a computer which is exemplified by a personal computer. The control apparatus 10 and the radiotherapy apparatus 3 are connected to each other to be possible for data to be transmitted bidirectionally.

The radiotherapy apparatus 3 is provided with an O-ring 12, a travelling gantry 14 and a therapeutic radiation irradiating unit 16. The O-ring 12 is formed like a ring and is supported to a base to be rotatable around a rotation axis 17. The rotation axis 17 is parallel to a vertical direction. The travelling gantry 14 is formed like a ring, is arranged inside the O-ring 12, and is supported by the O-ring 12 to be rotatable around a rotation axis 18. The rotation axis 18 is orthogonal to the vertical direction and passes an isocenter 19 which is contained in the rotation axis 17. The rotation axis 18 is fixed to the O-ring 12, i.e., rotates around the rotation axis 17 together with the O-ring 12.

The therapeutic radiation irradiating unit 16 is arranged inside the travelling gantry 14. The therapeutic radiation irradiating unit 16 is supported by the travelling gantry 14 to be rotatable around a tilt axis 21 and moreover to be rotatable around a pan axis 22. The pan axis 22 is fixed to the travelling gantry 14 and is parallel to the rotation axis 18 without intersecting the rotation axis 18. The tilt axis 21 and the pan axis 22 are orthogonal to each other. The intersection point of the tilt axis 21 and the pan axis 22 is apart from the isocenter 19 by about 1 m.

Moreover, the radiotherapy apparatus 3 is provided with a rotation drive unit 11, a swinging unit 15 and a travelling drive unit (not shown). The rotation drive unit 11 is controlled by the control apparatus 10 to rotate the O-ring 12 around the rotation axis 17. Moreover, the rotation drive unit 11 measures a rotation angle of the O-ring 12 to the base and outputs the measured rotation angle to the control apparatus 10. The travelling drive unit is controlled by the control apparatus 10 to rotate the travelling gantry 14 around the rotation axis 18. Moreover, the travelling drive unit measures a gantry angle of the travelling gantry 14 to the O-ring 12 and outputs the measured gantry angle to the control apparatus 10.

The swinging unit 15 is controlled by the control apparatus 10 to turn the therapeutic radiation irradiating unit 16 around the tilt axis 21 and to turn the therapeutic radiation irradiating unit 16 around the pan axis 22. Moreover, the swinging unit 15 measures a tilt angle of the therapeutic radiation irradiating unit 16 to the travelling gantry 14 around tilt axis 21 and outputs the measured tilt angle to the control apparatus 10. Moreover, the swinging unit 15 measures a pan angle of the therapeutic radiation irradiating unit 16 to the travelling gantry 14 around the pan axis 22 and outputs the measured pan angle to the control apparatus 10.

The therapeutic radiation irradiating unit 16 is controlled by the control apparatus 10 to irradiate a therapeutic radiation 23. The therapeutic radiation 23 is a cone beam having a point of intersection of the pan axis 22 and the tilt axis 21 as a vertex. The therapeutic radiation 23 is formed to have a uniform intensity distribution. The therapeutic radiation irradiating unit 16 is provided with a multi-leaf collimator 20. The multi-leaf collimator 20 is fixed on the therapeutic radiation irradiating unit 16 and is arranged in an irradiation region of the therapeutic radiation 23. The multi-leaf collimator 20 is controlled by the control apparatus 10 to shield a part of the therapeutic radiation 23 and adjust the shape of the radiation field when the therapeutic radiation 23 is irradiated to the patient.

In this way, because the therapeutic radiation irradiating unit 16 is supported by the travelling gantry 14 and the therapeutic radiation irradiating unit 16 is fixed on the travelling gantry 14 to turn to the isocenter 19, the therapeutic radiation 23 always passes the isocenter 19 even if the rotation drive unit 11 rotates the O-ring 12 or the travelling drive unit rotates the travelling gantry 14. That is, the irradiation of the therapeutic radiation 23 from an optional direction for the isocenter 19 through the travelling and the rotation is made possible.

Moreover, the radiotherapy apparatus 3 is provided with a plurality of imager systems. That is, the radiotherapy apparatus 3 is provided with a first diagnostic X-ray source 24, a second diagnostic X-ray source 25, a first sensor array 32 and a second sensor array 33. The first diagnostic X-ray source 24 is supported by the travelling gantry 14, and is arranged inside the travelling gantry 14 such that an angle between a line which links the first diagnostic X-ray source 24 and the isocenter 19 and a line which links the therapeutic radiation irradiating unit 16 and the isocenter 19 is an acute angle. The second diagnostic X-ray source 25 is supported by the travelling gantry 14, and is arranged inside the travelling gantry 14 such that an angle between a line which links the second diagnostic X-ray source 25 and the isocenter 19 and a line which links the therapeutic radiation irradiating unit 16 and the isocenter 19 is an acute angle. Moreover, the second diagnostic X-ray source 25 is arranged such that an angle between the line which links the first diagnostic X-ray source 24 and the isocenter 19 and the line which links the second diagnostic X-ray source 25 and the isocenter 19 is a right angle (90 degrees). The first sensor array 32 is supported by the travelling gantry 14 and is arranged to be opposite to the first diagnostic X-ray source 24 through the isocenter 19. The second sensor array 33 is supported by the travelling gantry 14 and is arranged to be oppose to the second diagnostic X-ray source 25 through the isocenter 19.

The first diagnostic X-ray source 24 is controlled by the control apparatus 10 to irradiate the first diagnostic X-ray 35 for the isocenter 19 at predetermined timings. The first diagnostic X-ray 35 is irradiated from one point of the first diagnostic X-ray source 24 and is a cone beam having the point as a vertex. The second diagnostic X-ray source 25 is controlled by the control apparatus 10 to irradiate the second diagnostic X-ray 36 for the isocenter 19 at predetermined timings. The second diagnostic X-ray 36 is irradiated from one point of the second diagnostic X-ray source 25 and is a cone beam having the point as a vertex.

The first sensor array 32 is provided with a light receiving section. The first sensor array 32 is controlled by the control apparatus 10 to generate a first transmissive image based on the X-ray that is received by the light receiving section. The second sensor array 33 is provided with a light receiving section. The second sensor array 33 is controlled by the control apparatus 10 to generate a second transmissive image based on the X-ray that is received by the light receiving section. The transmissive image is formed from a plurality of pixels. The plurality of pixels are arranged in a matrix on the transmissive image and are assigned with brightnesses, respectively. The brightness corresponding to each of the plurality of pixels of the transmissive image is colored to image a subject. FPD (Flat panel Detector), X-ray II (Image Intensifier) are exemplified as the first sensor array 32 and the second sensor array 33.

According to such imager systems, the transmissive image centered on the isocenter 19 can be generated based on image signals acquired by the first sensor array 32 and the second sensor array 33.

Moreover, the radiotherapy apparatus 3 is provided with a couch 41 and a couch drive unit 42. The couch 41 is supported to the base to be rotatable around each of the x-axis, the y-axis and the z-axis and to be movable in parallel to each of the x-axis, the y-axis and the z-axis. Here, the x-axis, the y-axis and the z-axis are orthogonal to each other. The patient 43 to be cured by the radiotherapy system lies on the couch 41. The couch 41 is provided with a fixture (not shown). The fixture fixes the patient 43 on the couch 41 so as not for the patient 43 to move. The couch drive unit 42 is controlled by the control apparatus 10 to rotate the couch 41 and to move the couch 41 in parallel to any of the above axes.

Figure 2:
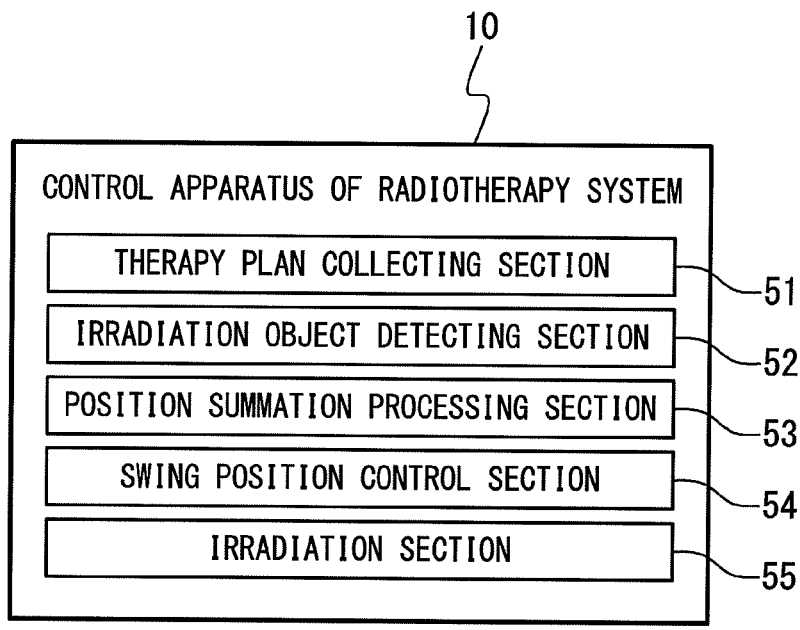
FIG. 2 is a block diagram showing a control apparatus of a radiotherapy system.

FIG. 2 shows the control apparatus 10. The control apparatus 10 is a computer and is provided with a CPU, a storage unit, a removal memory drive, a communication unit, an input unit, an output unit and interfaces (not shown). The CPU executes a computer program which is installed in the control apparatus 10 and controls the storage unit, the removal memory drive, the communication unit, the input unit and the output unit. The storage unit stores the computer program, information generated by the CPU, and information used by the CPU. The removal memory drive is used to read data which has been recorded on a storage medium when the storage medium is inserted therein. The removal memory drive is especially used to install the computer program in the control apparatus 10 when the storage medium storing a computer program is inserted. The communication unit is used to receive information which is transmitted from another computer connected with the control apparatus 10 through a communication network. Especially, the communication unit is used to download a computer program from the other computer and to install the computer program in the control apparatus 10. The input unit outputs data generated through an operation by the user to the CPU. As the input unit, a keyboard and a mouse are exemplified. The output unit outputs information generated by the CPU to be recognizable to the user. As the output unit, a display which displays an image generated by the CPU is exemplified.

The interface outputs information generated by an external unit connected with the control apparatus 10 to the CPU, and outputs information generated by the CPU to the external unit. The external units contain the rotation drive unit 11, the travelling drive unit, the swinging unit 15, the therapeutic radiation irradiating unit 16, the multi-leaf collimator 20, the first diagnostic X-ray source 24, the second diagnostic X-ray source 25, the first sensor array 32, the second sensor array 33, and the couch drive unit 42 of the radiotherapy apparatus 3.

The computer program which is installed in the control apparatus 10 is formed from a plurality of computer programs to make the control apparatus 10 realize a plurality of functions, respectively. The plurality of functions contain a therapy plan collecting section 51, an irradiation object detecting section 52, a position summation processing section 53, a swing position control section 54 and an irradiation section 55.

The therapy plan collecting section 51 collects a therapy plan from the input unit. The therapy plan shows combinations of an irradiation angle and a dose. The irradiation angle shows a direction of irradiation of the therapeutic radiation 23 to the affected part of the patient 43 and contains a couch position, the O-ring rotation angle, and a gantry rotation angle. The couch position shows a position of the couch 41 to the base. The O-ring rotation angle shows a position of the O-ring 12 to the base. The gantry rotation angle shows a position of the travelling gantry 14 to the O-ring 12. The dose shows a dose of the therapeutic radiation 23 which is irradiated to the patient 43 at the irradiation angle.

The irradiation object detecting section 52 controls the couch drive unit 42 such that the couch 41 is arranged in the couch position shown in the therapy plan, that is, the affected part of the patient 43 is arranged almost at the isocenter 19. Moreover, the irradiation object detecting section 52 controls the rotation drive unit 11 such that the O-ring 12 is arranged in the O-ring rotation angle shown in the therapy plan. Moreover, the irradiation object detecting section 52 controls the travelling drive unit of the radiotherapy apparatus 3 such that the travelling gantry 14 is arranged in the gantry rotation angle shown in the therapy plan.

The irradiation object detecting section 52 controls the first diagnostic X-ray source 24 such that the first diagnostic X-ray 35 is irradiated to the patient 43 periodically (in a 50-ms interval), after the couch 41, the O-ring 12 and the travelling gantry 14 are arranged in given positions shown in the therapy plan. Moreover, the irradiation object detecting section 52 controls the second diagnostic X-ray source 25 such that the second diagnostic X-ray 36 is irradiated to the patient 43 periodically at a plurality of times at which the first diagnostic X-ray 35 is irradiated. Moreover, the irradiation object detecting section 52 controls the first sensor array 32 such that a plurality of first transmissive images are generated based on the X-ray which has transmitted the patient 43 when the first diagnostic X-ray 35 is irradiated to the patient 43. Moreover, the irradiation object detecting section 52 controls the second sensor array 33 such that a plurality of second transmissive images are generated based on the X-ray which has transmitted the patient 43 when the second diagnostic X-ray 36 is irradiated to the patient 43.

The irradiation object detecting section 52 calculates a plurality of specific part positions based on the plurality of first transmissive images and the plurality of second transmissive images. The plurality of specific part positions respectively show positions where the affected part of the patient 43 is positioned at the plurality of times at which the first diagnostic X-ray 35 (the second diagnostic X-ray 36) is irradiated. That is, the irradiation object detecting section 52 calculates the specific part position at which the affected part of the patient 43 is positioned based on the first transmissive image and the second transmissive image every time the first transmissive image and the second transmissive image are imaged.

Moreover, the irradiation object detecting section 52 calculates a target position based on the specific part positions. The target position shows a position where the affected part of the patient 43 will be positioned at a time of 50 ms after the first transmissive image and the second transmissive image are imaged.

The position summation processing section 53 controls the swinging unit 15 to measure a direction of the therapeutic radiation irradiating unit 16 at a current time. The direction contains the tilt angle and the pan angle with respect to the therapeutic radiation irradiating unit 16. That is, the position summation processing section 53 controls the swinging unit 15 to measure the tilt angle and the pan angle with respect to the therapeutic radiation irradiating unit 16, and calculates the direction of the therapeutic radiation irradiating unit 16 at the current time based on the measured tilt angle and the measured pan angle.

The swing position control section 54 calculates an operation amount based on the target position calculated by the irradiation object detecting section 52. The swinging unit 15 drives the therapeutic radiation irradiating unit 16 to turn around the tilt axis 21 and the pan axis 22 based on the operation amount. At this time, the swing position control section 54 calculates the operation amount in a sampling period (for example, 5 ms) which is sufficiently short than the measurement period of the plurality of first transmissive images by the irradiation object detecting section 52.

The irradiation section 55 controls the therapeutic radiation irradiating unit 16 such that the therapeutic radiation 23 is irradiated when a difference between the direction to which the therapeutic radiation irradiating unit 16 is directed by the swing position control section 54, and an actual direction of the therapeutic radiation irradiating unit 16 falls within a predetermined range.

Figure 3:
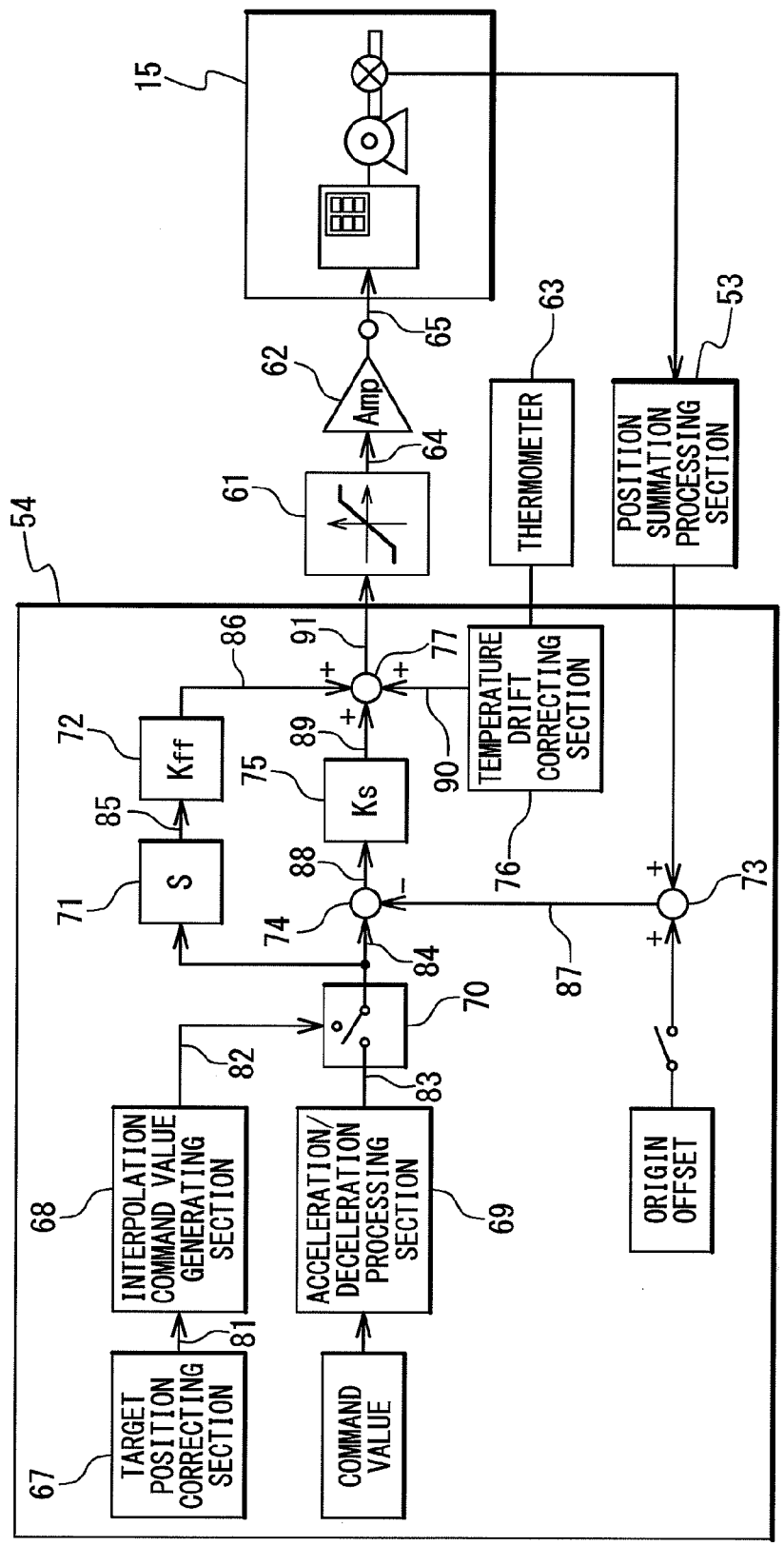
FIG. 3 is a block diagram showing a swing position control section.

Moreover, the radiotherapy apparatus 3 is further provided with a D/A conversion circuit 61, an amplifier 62 and a thermometer 63, as shown in FIG. 3. The D/A conversion circuit 61 generates a control electric signal 64 with a voltage corresponding to the operation amount calculated by the control apparatus 10. The amplifier 62 outputs an electric signal 65 by amplifying the voltage of the control electric signal 64. The D/A conversion circuit 61 and the amplifier 62 are arranged on a distributor. The thermometer 63 measures a temperature of the distributor and outputs the measured temperature to the control apparatus 10.

Moreover, FIG. 3 shows the swing position control section 54. The swing position control section 54 is provided with a target position correcting section 67, an interpolation command value generating section 68, an acceleration/deceleration processing section 69, a switch 70, a differentiating section 71, a feed-forward section 72, an adder 73, an adder 74, an operation amount calculating section 75, a temperature drift correcting section 76, and an adder 77.

The target position correcting section 67 calculates a coefficient based on the time at which the first transmissive image and the second transmissive image have been imaged, which are used to calculate the target position which is calculated by the irradiation object detecting section 52. The target position correcting section 67 calculates a post-correction target position 81 based on the coefficient and the target position calculated by the irradiation object detecting section 52. The interpolation command value generating section 68 calculates an interpolation command value 82 based on the post-correction target position 81. At this time, the interpolation command value 82 is calculated for every sampling period (e.g. 5 ms) which is sufficiently short compared with the measurement period that the post-correction target position 81 is calculated (e.g. 50 ms).

The acceleration/deceleration processing section 69 outputs a post-correction command value 83. The post-correction command value 83 indicates a position of the isocenter 19.

The switch 70 calculates the command value 84 based on information supplied to the control apparatus 10 through the input unit. The command value 84 shows the interpolation command value 82 when one of the interpolation command value 82 and the post-correction command value 83 is selected, and when tracking is carried out, and the command value 84 shows the post-correction command value 83 when not tracking.

The differentiating section 71 calculates a velocity 85 based on the command value 84. The velocity 85 shows a change amount of the command value 84 for every unit time. The feed-forward section 72 calculates a feed-forward operation amount 86 based on the velocity 85.

The adder 73 calculates a position result value 87 based on a position measured by the position accumulation processing section 53. The position result value 87 shows a value obtained by adding an origin offset value to the position measured by the position accumulation processing section 53. The adder 74 calculates a position deviation 88 based on the command value 84 and the position result value 87. The position deviation 88 shows a difference obtained by subtracting the position result value 87 from the command value 84.

The operation amount calculating section 75 calculates an operation amount 89 based on the position deviation 88. The temperature drift correcting section 76 calculates a temperature drift correction amount 90 based on a temperature measured by the thermometer 63. The adder 77 calculates an operation amount 91 based on the feed-forward operation amount 86, the operation amount 89 and the temperature drift correction amount 90. The operation amount 91 shows a summation obtained by adding the feed-forward the operation amount 86, the operation amount 89, and the temperature drift correction amount 90.

Figure 4:
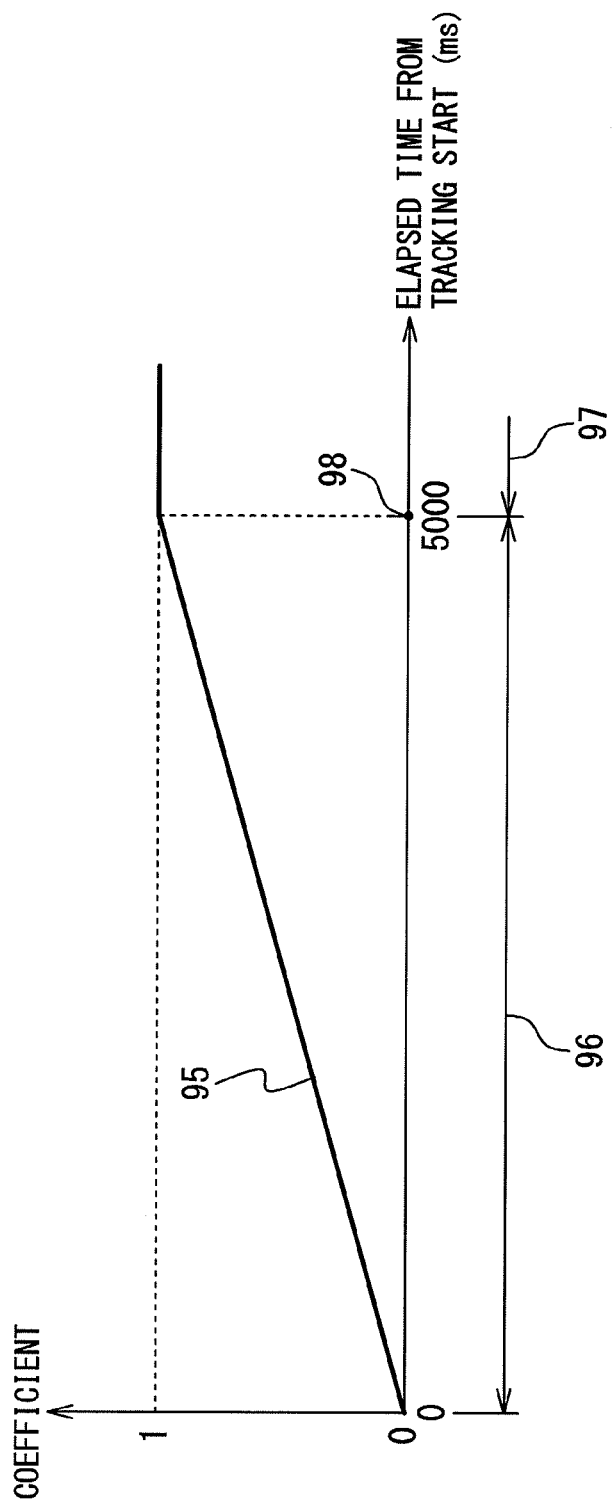
FIG. 4 is a graph showing a change of a coefficient calculated by a target position correcting section.

FIG. 4 shows a change of the coefficient calculated by the target position correcting section 67. The change 95 shows that the period during which the coefficient is calculated contains a preparation period 96 and a therapy period 97. The preparation period 96 is a period prior to a separation time 98 of the period during which the coefficient is calculated. The therapy period 97 is a period after the separation time 98 of the period during which the coefficient is calculated. The separation time 98 is a time after 5000 ms from the time when tracking is started. Moreover, the change 95 shows that the time when the tracking is started is time 0. Moreover, the change 95 shows increase proportional to the elapsed time in the preparation period 96. Moreover, the change 95 shows "1" in the therapy period 97.

At this time, the post-correction target position 81 calculated by the target position correcting section 67 indicates an internal division position in a segment which links the target position calculated by the irradiation object detecting section 52 and the isocenter 19. The internal division ratio based on the internal division position shown by the post-correction target position 81 is equal to a coefficient. That is, the post-correction target position 81 indicates the isocenter 19 when the coefficient is "0" and the target position calculated by the irradiation object detecting section 52 when the coefficient shows "1". It should be noted that the above segment may be substituted by another segment which links another position different the isocenter 19 and the target position. As the other position different from the isocenter 19, a position to which the radiation irradiating unit 16 directs at time of start of tracking is exemplified.

Figure 5:
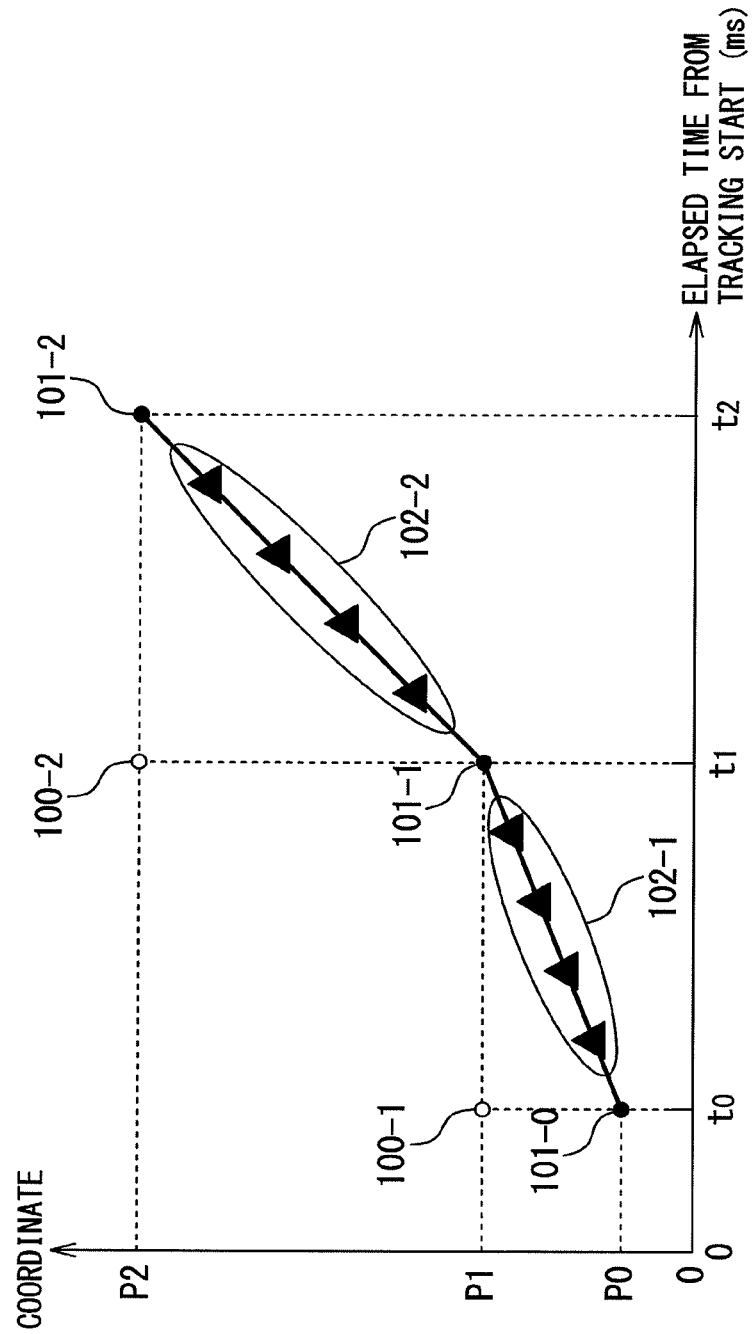
FIG. 5 is a graph showing an interpolation command value calculated by an interpolation command value generating section.

FIG. 5 shows an interpolation command value 82 which is calculated by the interpolation command value generating section 68. The interpolation command value 82 contains a plurality of interpolation command values corresponding to a plurality of times every sampling period. The interpolation command value 101-0 corresponding to time t0 among the plurality of interpolation command values is equal to the post-correction target position which is calculated by the target position correcting section 67 at a time earlier by the measurement period (50 ms) than the time t0. The interpolation command value 101-1 corresponding to time t1 among the plurality of interpolation command values is equal to the post-correction target position 100-1 which is calculated by the target position correcting section 67 at the time t0 earlier by the measurement period (50 ms) than the time t1. The interpolation command value 101-2 corresponding to time t2 among the plurality of interpolation command values is equal to the post-correction target position 100-2 which is calculated by the target position correcting section 67 at the time t1 earlier by the measurement period than the time t2.

The plurality of interpolation command values 102-1 in unit times during the period from the time t0 to the time t1 among the plurality of interpolation command values are interpolated in a constant change from the interpolation command value 101-0 and the interpolation command value 101-1. The plurality of interpolation command values 102-2 corresponding to the period from the time t1 to the time t2 among the plurality of interpolation command values are interpolated from the interpolation command value 101-1 and the interpolation command value 101-2.

Figure 6:
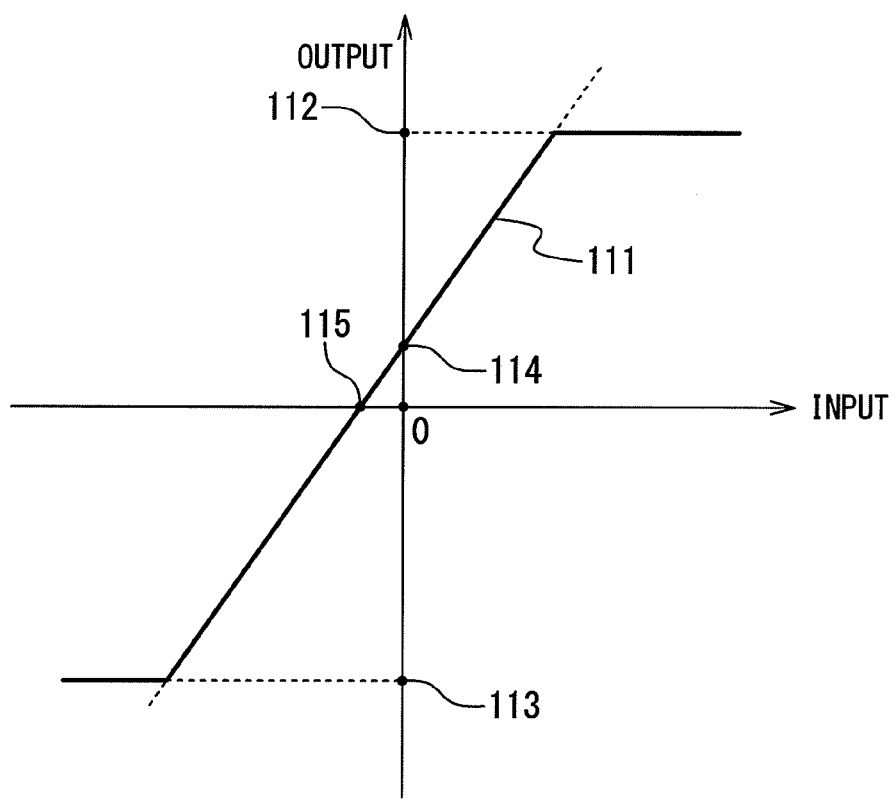
FIG. 6 is a graph showing a relation between an input and an output of a D/A converting circuit.

FIG. 6 shows a relation between the input and the output in the distributor which is formed from the D/A conversion circuit 61 and the amplifier 62. The relation 111 shows that the output increases constantly to the input and it shows that the output is almost proportional to the input. Moreover, the relation 111 shows that the output has a maximum value 112 and that the output has a minimum value 113. Moreover, the relation 111 shows that the output shows a value 114 different from "0" when the input shows "0" and that the input shows a value 115 which is different from "0" when the output shows "0". The value 114 and the value 115 change depending on the temperature of the distributor.

At this time, the temperature drift correcting section 76 stores how the value 115 changes depending on the temperature of the distributor in the storage. Also, the temperature drift correcting section 76 calculates the temperature drift correction amount 90 such that the voltage of the control electrical signal 64 show 0V, when a summation of the operation amount 89 and the feed-forward operation amount 86 shows "0" based on the temperature of the distributor measured by the thermometer 63. That is, the temperature drift correction amount 90 shows a value obtained by multiplying −1 by a value 115 corresponding to the temperature of the distributor measured by the thermometer 63.

According to such a control, the control apparatus 10 can perform the control so as to prevent the drive more surely when a summation of the operation amount 89 and the feed-forward operation amount 86 shows "0", or when a value below a specified value is shown, that is, when it is not necessary to drive the swinging unit 15.

Figure 7:
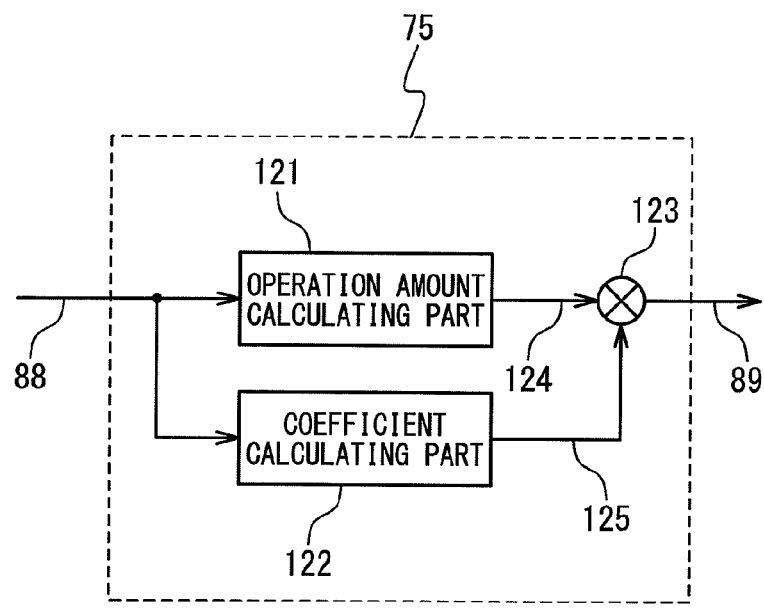
FIG. 7 is a block diagram showing an operation amount calculating section.

FIG. 7 shows the operation amount calculating section 75. The operation amount calculating section 75 is provided with an operation amount calculating part 121, a coefficient calculating part 122 and a multiplier 123. The operation amount calculating part 121 calculates a pre-correction operation amount 124 based on the position deviation 88. A well-known method can be applied for such calculation. The coefficient calculating part 122 calculates a coefficient 125 based on the position deviation 88. The multiplier 123 calculates the operation amount 89 obtained as the output of the operation amount calculating section 75 based on pre-correction operation amount 124 and the coefficient 125. The operation amount 89 shows a product of the coefficient 125 and pre-correction operation amount 124.

Figure 8:
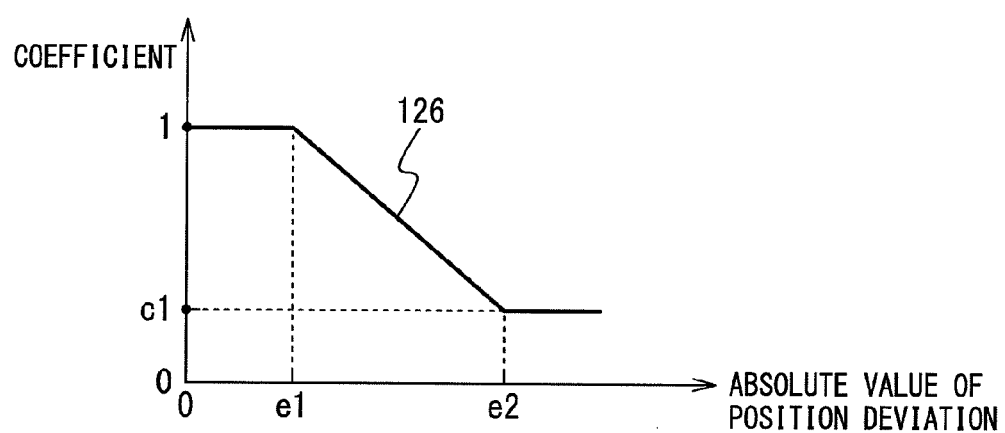
FIG. 8 is a graph showing a relation between a position deviation and the coefficient.

FIG. 8 shows a relation of the position deviation 88 and the coefficient 125. The relation 126 shows that the coefficient 125 decreases constantly with respect to the absolute value of the position deviation 88. Moreover, the relation 126 shows that the coefficient 125 is "1" when the absolute value of the position deviation 88 is equal to or less than a value e1. Moreover, the relation 126 shows that the coefficient 125 decreases with the increase of position deviation 88 when the absolute value of position deviation 88 is between the value e1 and a value e2. Moreover, the relation 126 shows that the coefficient 125 shows a value c1 when the absolute value of position deviation 88 is equal to or more than the value e2. The value c1 is set such that the driving force which is generated by the swinging unit 15 is larger than a static friction when the radiation irradiating unit 16 rotates.

According to such a coefficient 125, when the position deviation 88 is large, the operation amount 89 does not become large too much. Therefore, the control apparatus 10 can move the therapeutic radiation irradiating unit 16 more stably by using the swinging unit 15 when the position deviation 88 is large. Therefore, compared with a conventional control apparatus of a radiotherapy system that the swinging unit 15 is controlled based on the pre-correction operation amount 124, the control apparatus 10 can make the operation amount 89 small when the position deviation 88 is large. Also, the radiation irradiating unit 16 can be turned stably by using the swinging unit 15, and the swinging unit 15 can be controlled in a higher accuracy.

An operation method of the radiotherapy system of the present invention is performed by the control apparatus 10. At first, the user inputs a therapy plan prepared previously through the input unit to the control apparatus 10. The therapy plan shows combinations of an irradiation angle and a dose. The irradiation angle shows a direction when the therapeutic radiation 23 is irradiated to the affected part of the patient 43, and contains the couch position, and the O-ring rotation angle and the gantry rotation angle. The couch position shows a position and the direction of the couch 41 to the base. The O-ring rotation angle shows a position of the O-ring 12 to the base. The gantry rotation angle shows the angular position of the travelling gantry 14 to the O-ring 12. The dose shows a dose of the therapeutic radiation 23 which is irradiated to the patient 43 at each of the irradiation angles.

The user fixes the patient 43 on the couch 41 of the radiotherapy apparatus 3. The control apparatus 10 controls the couch drive unit 42 so that the couch 41 is positioned on a couch position shown by the therapy plan. Moreover, the control apparatus 10 controls the rotation drive unit 11 so that the O-ring 12 is positioned on the O-ring rotation angle which the therapy plan shows. Moreover, the control apparatus 10 controls the travelling drive unit of the radiotherapy apparatus 3 so that the travelling gantry 14 is positioned on the gantry rotation angle shown by the therapy plan.

The control apparatus 10 controls the first diagnostic X-ray source 24 to irradiate the first diagnostic X-ray 35 periodically (in the 50-ms interval) to the patient 43 after the couch 41, the O-ring 12 and the travelling gantry 14 are positioned on predetermined positions shown by the therapy plan. Moreover, the control apparatus 10 controls the second diagnostic X-ray source 25 to irradiate the second diagnostic X-ray 36 periodically to the patient 43 at the plurality of times at which the first diagnostic X-ray 35 is irradiated. Moreover, the control apparatus 10 controls the first sensor array 32 to generate a plurality of first transmissive images based on the X-ray which has transmitted the patient 43 when the first diagnostic X-ray 35 has been irradiated to the patient 43. Moreover, the control apparatus 10 controls the second sensor array 33 to generate a plurality of second transmissive images based on the X-ray which has transmitted the patient 43 when the second diagnostic X-ray 36 has been irradiated to the patient 43.

The control apparatus 10 calculates a specific part position based on the first transmissive image and the second transmissive image generated at the time t0. The specific part position shows a location where the affected part of the patient 43 is positioned at the time t0. Moreover, the control apparatus 10 calculates the target position based on the specific part position. The target position shows a position where the affected part of the patient 43 is positioned at the time t1 after 50 ms from the time t0. The control apparatus 10 calculates the coefficient at the time t0 so as to match the change 95 shown in FIG. 4. The control apparatus 10 calculates the post-correction target position 100-1 based on the target position and the coefficient, as shown in FIG. 5. The post-correction target position 81 shows an internal division position of a segment which links the target position and the isocenter 19 based on ratios shown by the coefficient. The control apparatus 10 calculates the interpolation command value 101-1 and the plurality of interpolation command values 102-1 based on the post-correction target position 100-1.

The control apparatus 10 calculates the feed-forward operation amount 86 based on a change of the interpolation command value for every unit time.

The control apparatus 10 calculates the pre-correction operation amount 124 based on the position deviation 88 between the interpolation command value and the position measured by the swinging unit 15. Moreover, the control apparatus 10 calculates the coefficient 125 to match the relation 126 of FIG. 8. The control apparatus 10 calculates the operation amount 89 which shows a product of the coefficient 125 and the pre-correction operation amount 124.

The control apparatus 10 calculates the temperature drift correction amount 90 based on the temperature measured by the thermometer 63.

The control apparatus 10 calculates the operation amount 91 based on the feed-forward operation amount 86, the operation amount 89 and the temperature drift correction amount 90. The D/A conversion circuit 61 generates the control electrical signal 64 with a voltage corresponding to the operation amount 91. The amplifier 62 outputs the electrical signal 65 in which the voltage of the control electrical signal 64 is amplified. The D/A conversion circuit 61 and the amplifier 62 are arranged in the distributor. When being supplied with the electrical signal 65, the swinging unit 15 drives the radiation irradiating unit 16 to turn around the tilt axis 21 and the pan axis 22.

The control apparatus 10 controls the therapeutic radiation irradiating unit 16 not to irradiate the therapeutic radiation 23 when a current time is contained in the preparation period 96. The control apparatus 10 controls the therapeutic radiation irradiating unit 16 to irradiate the therapeutic radiation 23, when the current time is contained in the therapy period 97 and when a difference between the position shown by the interpolation command value and a position which the therapeutic radiation irradiating unit 16 turns at the current time is within a predetermined range. The control apparatus 10 controls the therapeutic radiation irradiating unit 16 not to irradiate the therapeutic radiation 23, when the difference between the position shown by the interpolation command value and the position which the therapeutic radiation irradiating unit 16 turns at the current time is not within the predetermined range. The control apparatus 10 controls the therapeutic radiation irradiating unit 16 repeatedly in units of the sampling periods, during each of which the interpolation command value is calculated.

Figure 9:
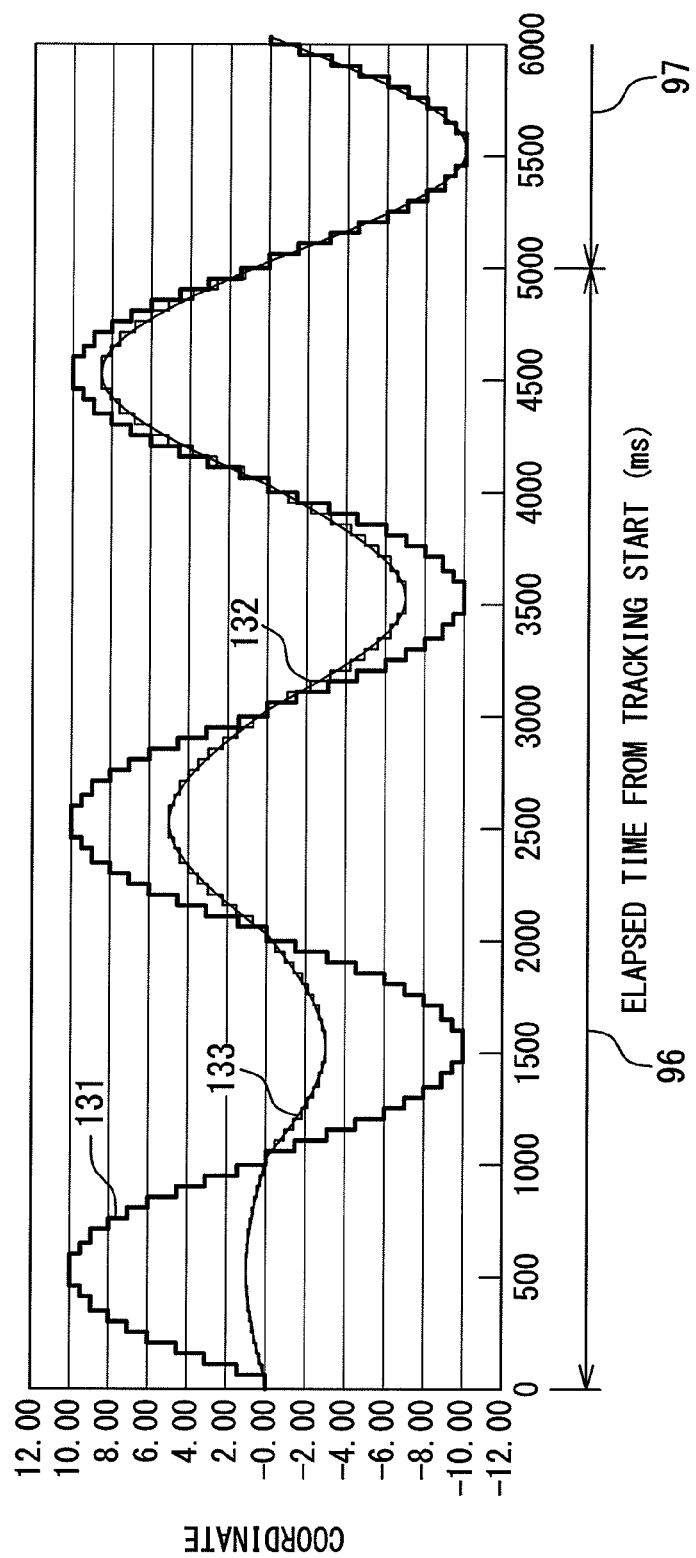
FIG. 9 is a graph showing a change of a target position, a change of a post-correction target position and a change of the interpolation command value.

FIG. 9 shows a change of the target position calculated based on the position of the affected part of the patient 43. A change 131 shows that the target position is calculated every measurement period (50 ms). Moreover, FIG. 9 shows the change of the post-correction target position calculated based on the target position. A change 132 shows that the post-correction target position changes gently in the preparation period 96 and that the post-correction target position matches the target position in the therapy period 97. Moreover, FIG. 9 shows the change of the interpolation command value calculated based on the post-correction target position. A change 133 shows that the interpolation command value is calculated at a period which is shorter than the measurement period (50 ms) during which the target position is calculated. Moreover, the interpolation command value changes gently in the preparation period 96 in change 133. Moreover, the change 133 shows that the target position matches the interpolation command value in the therapy period 97.

In order to irradiate the therapeutic radiation 23 only to the affected part of the patient 43, the radiation irradiating unit 16 has to turn to the affected part of the patient 43 more correctly in a shorter time, and the high responsibility is required for the swinging operation. In order to generally realize this, a control gain is made large. However, if the current position of the radiation irradiating unit 16 is largely displaced from the target position at the start of a tracking operation when the control gain is large, there is a possibility that overload is imposed to the motor of the swinging unit 15 so that the motor trip occurs.

According to the operation method of the radiotherapy system according to the present invention, the therapeutic radiation irradiating unit 16 is never controlled by the control apparatus 10 so as to move the therapeutic radiation irradiating unit 16 rapidly in the preparation period 96 when turning to the isocenter 19 at an initial stage. Therefore, even if the control apparatus 10 is in a condition to improve a responsibility by increasing the control gain large, it is prevented that a motor trip occurs in the swinging unit 15 in the preparation period 96.

Because the coefficient 125 changes as shown by the relation 126 in FIG. 8, the operation amount 89 does not become large too much even when the position deviation 88 is large. Therefore, the control apparatus 10 can move the radiation irradiating unit 16 more stably by using the swinging unit 15 when the position deviation 88 is large. Thus, the control apparatus 10 can turn the radiation irradiating unit 16 stably by using the swinging unit 15, compared with the well-known control unit of a radiotherapy system which is not provided with the coefficient calculating section 122 and the multiplier 123. The swinging unit 15 can be controlled in a higher accuracy.

Moreover, in the operation method of the radiotherapy system according to the present invention, the control apparatus 10 calculates the temperature drift correction amount 90 based on the temperature of the distributor measured by the thermometer 63. The control apparatus 10 can stop the swinging unit 15 more surely according to the temperature drift correction amount 90 when it is not necessary to drive the swinging unit 15.

The change which is different from the change 95 may be substituted for the coefficient calculated by the target position correcting section 67. It is sufficient that the coefficient shows "0" at the time of start of tracking, and the coefficient increases constantly with the elapsed time in the preparation period 96, and shows "1" in the therapy period 97. FIG. 10 shows an example of the change. A change 141 shows that the preparation period 96 contains a first period 142 and a second period 143. The first period 142 is a period prior to the separation time 144 in the preparation period 96. The second period 143 is a period after the separation time 144 in the preparation period 96. The separation time 144 is an optional time which belongs to the preparation period 96. The change 141 shows "0" at the time of start of tracking. Moreover, the change 141 shows constant increase to be convex downwardly in the first period 142. Moreover, the change 141 shows constant increase to be convex upwardly in the second period 143. Moreover, the change 141 shows "1" in the therapy period 97. The control apparatus 10 can prevent the motor trip of the swinging unit 15 from occurring in the preparation period 96 in which a responsibility is improved by increasing a control gain large, even in case of application of the change 141, like the above embodiments.

It should be noted that the control apparatus 10 can calculate the target position based on the specific part position which is calculated based on another sensor which is different from the imager system of the radiotherapy apparatus 3. As the sensor, an infrared camera is exemplified. At this time, the control apparatus 10 calculates the position of the affected part of the patient 43 based on the position of a marker on infrared image obtained by imaging the marker arranged on the body surface of the patient 43 by an infrared camera, and calculates the target position based on the calculated marker position. The control apparatus 10 can prevent a motor trip of the swinging unit 15 in the preparation period 96 in the state that a responsibility is improved by increasing a control gain, like the above embodiments even when such a sensor is applied.

The application claims a priority on convention based on Japanese Patent Application No. 2010-032853 filed on Feb. 17, 2010 and the disclosure thereof is incorporated herein by reference.

The invention claimed is:

1. A control apparatus of a radiotherapy system comprising:
an irradiation object detecting section configured to calculate a target position based on a position of a specific part of a sample at a measurement time; and
a swing position control section configured to control a drive unit to drive a radiation irradiating unit configured to irradiate a therapeutic radiation, such that said radiation irradiating unit turns to a post-correction target position at a control time after the measurement time, wherein said post-correction target position indicates a position nearer a position to which said radiation irradiating unit turns immediately before the control time rather than the target position, when the control time is contained in a preparation period, and wherein when the control time is contained in a therapy period after the preparation period, said post-correction target position shows the target position.

2. The control apparatus according to claim 1, wherein said post-correction target position indicates a position of an internal division of a segment linking an initial position and the target position when the control time is contained in the preparation period, and wherein a ratio of the internal division of the segment by said post-correction target position is calculated such that said post-correction target position gradually approaches to the target position with elapse of time.

3. The control apparatus according to claim 2, wherein a change per a unit time of the internal division ratio is constant.

4. The control apparatus according to claim 3, wherein said swing position control section comprises:

an operation amount calculating section configured to calculate an operation amount based on a position deviation between said post-correction target position and the position to which said radiation irradiating unit turns;

a coefficient calculating section configured to calculate a coefficient based on the position deviation; and a multiplier configured to calculate a post-correction operation amount by multiplying the operation amount by the coefficient, wherein the coefficient decreases constantly with respect to an absolute value of the position deviation, and wherein said drive unit is controlled based on the post-correction operation amount.

5. The control apparatus according to claim 4, wherein said swing position control section further comprises:

a feed-forward section configured to calculate a feed-forward operation amount based on a change of said post-correction target position, and wherein said drive unit is controlled based on the feed-forward operation amount in addition to the post-correction operation amount.

6. The control apparatus according to claim 5, wherein said swing position control section further comprises:

a temperature drift correcting section configured to calculate a temperature drift amount based on a temperature of a unit which generates an electrical signal supplied to said drive unit when said drive unit is controlled, and wherein said drive unit is controlled based on the temperature drift amount in addition to the feed-forward operation amount and the post-correction operation amount.

7. An operation method of a radiotherapy system, comprising:

calculating a target position based on a position of a specific part of a sample at a measurement time; and controlling a drive unit to drive a radiation irradiating unit which irradiates a therapeutic radiation, such that said radiation irradiating unit turns to a post-correction target position at a control time after the measurement time, wherein said post-correction target position indicates a position nearer a position to which said radiation irradiating unit turns immediately before the control time rather than the target position, when the control time is contained in a preparation period, and wherein when the control time is contained in a therapy period after the preparation period, said post-correction target position shows the target position.

8. The operation method of the radiotherapy system according to claim 7, wherein said post-correction target position indicates a position of an internal division of a segment linking an initial position and the target position when the control time is contained in the preparation period, and wherein a ratio of the internal division of the segment by said post-correction target position is calculated such that said post-correction target position gradually approaches to the target position with elapse of time.

9. The operation method of the radiotherapy system according to claim 8, wherein a change per a unit time of the internal division ratio is constant.

10. The operation method of the radiotherapy system according to claim 9, further comprising:

calculating an operation amount based on a position deviation between said post-correction target position and the position to which said radiation irradiating unit turns;

calculating a coefficient based on the position deviation; and calculating a post-correction operation amount by multiplying the operation amount by the coefficient, wherein the coefficient decreases constantly with respect to an absolute value of the position deviation, and wherein said drive unit is controlled based on the post-correction operation amount.

11. The operation method of the radiotherapy system according to claim 10, further comprising:

calculating a feed-forward operation amount based on a change of said post-correction target position, and wherein said drive unit is controlled based on the feed-forward operation amount in addition to the post-correction operation amount.

12. The operation method of the radiotherapy system according to claim 11, further comprising:

calculating a temperature drift amount based on a temperature of a unit which generates an electrical signal supplied to said drive unit when said drive unit is controlled, and wherein said drive unit is controlled based on the temperature drift amount in addition to the feed-forward operation amount and the post-correction operation amount.

* * * * *